United States Patent
Berman et al.

(10) Patent No.: US 8,107,592 B2
(45) Date of Patent: *Jan. 31, 2012

(54) METHOD OF RECONSTRUCTING COMPUTED TOMOGRAPHY (CT) VOLUMES SUITABLE FOR EXECUTION ON COMMODITY CENTRAL PROCESSING UNITS (CPUS) AND GRAPHICS PROCESSORS, AND APPARATUS OPERATING IN ACCORD WITH THOSE METHODS (ROTATIONAL X-RAY ON GPUS)

(75) Inventors: Ari P. Berman, Lexington, MA (US); Scott A. Thieret, Nashua, NH (US); Joseph Goddard, Salem, MA (US)

(73) Assignee: PME IP Australia Pty Ltd., Richmond, Victoria (AU)

( * ) Notice: Subject to any disclaimer, the term of this patent is extended or adjusted under 35 U.S.C. 154(b) by 0 days.

This patent is subject to a terminal disclaimer.

(21) Appl. No.: 12/831,510

(22) Filed: Jul. 7, 2010

(65) Prior Publication Data

US 2010/0272342 A1 Oct. 28, 2010

Related U.S. Application Data

(62) Division of application No. 11/264,287, filed on Nov. 1, 2005, now Pat. No. 7,778,392.

(60) Provisional application No. 60/624,465, filed on Nov. 2, 2004.

(51) Int. Cl.
*A61B 6/03* (2006.01)

(52) U.S. Cl. ............... 378/210; 378/4; 378/901

(58) Field of Classification Search ............... 378/205, 378/4, 210, 905; 345/424, 426, 506, 586
See application file for complete search history.

(56) References Cited

U.S. PATENT DOCUMENTS

| | | | | |
|---|---|---|---|---|
| 5,442,674 | A * | 8/1995 | Picard et al. | 378/20 |
| 6,236,704 | B1 * | 5/2001 | Navab et al. | 378/4 |

OTHER PUBLICATIONS

Stevens et al., Alignment of a volumetric tomography system, 2001, Medical Physics, vol. 28, No. 7, pp. 1472-1481.*
Navab et al., 3D Reconstruction from Projection Matrices in a C-Arm Based 3D-Angiography System, 1998, MICCAI'98, LNCS 1496, pp. 119-129.*

* cited by examiner

*Primary Examiner* — Edward Glick
*Assistant Examiner* — John Corbett
(74) *Attorney, Agent, or Firm* — Vierra Magen Marcus & DeNiro LLP

(57) ABSTRACT

The invention provides in one aspect methods and apparatus for use with C-arm and other CT systems, e.g., with non-rigid geometries. In such systems, by way of example, calibration can be performed to determine the exact position of the x-ray source and the exact orientation of the detector where each projection measurement is made. Next, a weighting coefficient can be determined for the voxels in each plane of a reconstruction volume at every possible projection. Finally, the order in which to process the voxels during image reconstruction can be determined. Following an actual CT scan procedure in which scans are obtained of a volume to be constructed, a system according to these and related aspects of the invention can use an optimal, pre-calculated processing method, while utilizing offsets and weighting coefficients determined during calibration, for performing backprojection image reconstruction.

9 Claims, 10 Drawing Sheets

METHOD OF RECONSTRUCTING COMPUTED TOMOGRAPHY (CT) VOLUMES SUITABLE FOR EXECUTION ON COMMODITY CENTRAL PROCESSING UNITS (CPUS) AND GRAPHICS PROCESSORS, AND APPARATUS OPERATING IN ACCORD WITH THOSE METHODS (ROTATIONAL X-RAY ON GPUS)

CROSS REFERENCE TO RELATED APPLICATIONS

This application is a divisional application of U.S. patent application Ser. No. 11/264,287, "METHOD OF RECONSTRUCTING COMPUTED TOMOGRAPHY (CT) VOLUMES SUITABLE FOR EXECUTION ON COMMODITY CENTRAL PROCESSING UNITS (CPUS) AND GRAPHICS PROCESSORS, AND APPARATUS OPERATING IN ACCORD WITH THOSE METHODS (Rotational X-Ray on GPUs)," filed on Nov. 1, 2005, by Berman, et al., issued as U.S. Pat. No. 7,778,392 on Aug. 17, 2010, which claims priority to U.S. Provisional Application No. 60/624,465, filed Nov. 2, 2004, both of which are incorporated herein by reference.

BACKGROUND OF THE INVENTION

The present invention relates to digital data processing and, particularly, to computed tomography (CT). It has application, by way of non-limiting example, in systems and methods of CT volume reconstruction by use of backprojection on central processing units (CPUs) and graphic processing units (GPUs), e.g., in health care (and more particularly, by way of non-limiting example, in medical diagnostics), defense, airline, and biology industries, to name but a few.

A computerized axial tomography (CAT) or computed tomography (CT) scan is a procedure used for visualizing features throughout the interior of opaque solid objects. The most traditional use is for imaging the human body as a medical diagnostic tool. CT scanning also has applicability to a variety of other industries including, but not limited to, defense, airline, and biology industries. A typical CT scan system is formed of a radiation source, such as an x-ray tube, a radiation detector, and a computer system. The radiation source and detector are positioned on opposite sides of an object to image. A beam of radiation is then projected from the source towards the detector, and those photons not absorbed in the object are transmitted toward and impact on the detector. The result is an image on the detector that represents a two-dimensional projection image of the object from the current position. The source and radiation detector are rotated around the object, typically 180° or 360°, during which the imaging process is repeated at a number of intermediate positions, so that a series of two-dimensional images of the object over a range of angular orientations is acquired. A series of these projection images is then fed from the detector into the computer system. The computer system can then use these two-dimensional projections to create various reconstructions of the object.

This concept is known as image reconstruction, and there are a variety of mathematical algorithms that can be used to accomplish this. Feldkamp backprojection, algebraic reconstruction technique (ART), and maximum likelihood expectation maximization (MLEM) are three such examples. Most algorithms are based on the assumption that a large number of projection measurements are made, such that every point in the object is included in radiation paths from many angles.

Feldkamp backprojection is a common reconstruction technique in which projection data is first convolved with a filter, and each view is successively superimposed over a square grid, which represents the volume that was imaged, at an angle that corresponds to its acquisition angle.

One example of backprojection is illustrated in U.S. Pat. No. 6,324,241, entitled, "Method and apparatus for CT reconstruction," which is said to describe a method for reconstructing a scanned CT image that includes the steps of acquiring projection data of an object by use of a flat-panel detector and filtering and back projecting the projection data in order to reconstruct a three-dimensional image of the object. That patent purports to provide for direct fan-parallel and three-dimensional reconstruction of computed tomographic images, without loss of resolution associated with radial interpolation, while retaining imaging quality and backprojection speed gains associated with parallel reconstruction.

While the '241 patent is among the prior art that provides means for performing backprojections, depending on the size of the object to image and the number of projections acquired, filtered backprojection can be a time- and computation-intensive process. Presently, the time required for most CT scan systems to perform acquisition and reconstruction of an 512×512×512 voxel object reconstructed from a collection of (500) 512×512 projection images is in the order of one hour, on a high-end workstation.

Conventional spiral CT scan machines have large, extremely rigid toroidal-shaped gantries. To image an object or a patient, the patient is passed through the machine via a moving table. The radiation source and detector(s) travel around the gantry and completely encircle the object or patient while it is moved through the machine. While conventional CT scanners are still widely used, they have a number of drawbacks. The closed toroidal shape of the gantry does not allow a physician easy access to a patient while the patient is in the imaging device. Furthermore, conventional CT scanners are large and very expensive machines. An alternative design is a free standing, C-arm-based CT scanning system, in which the radiation source and detector are suspended masses attached to an open C-arm that moves in an orbit around the patient in a variety of orientations. C-arm-based systems are smaller and less expensive than are conventional CT scan machines. However, because the source and detector of C-arm-based CT scanning systems are supported by fairly long arms (a typical C-arm arc has about a 6-foot diameter), as the system rotates around the object to image, the movements of the source and detector do not conform rigidly to a perfectly circular orbit. The location of the source can be modeled to have just three degrees of freedom; however, the orientation of the detector must also be considered, so that it moves effectively with six degrees a freedom. This creates a problem, as the trajectory of the source and the detector rarely represent a true circular orbit, which is a requirement for using Feldkamp backprojection image reconstruction. Therefore, acquired projection data might be different from that which was expected.

It is therefore an object of this invention to provide improved methods and apparatus for digital data processing and more particularly, computed tomography.

A related object of the invention is to provide such methods and apparatus as improve the speed at which CT computer systems perform three-dimensional reconstruction, particularly, for example, by backprojection.

It is yet another object of this invention to provide such methods and apparatus as maintain a cost-effective approach when the CT computer system is used in processing.

A further object of the invention is to provide such methods and apparatus as are suitable for use with non-rigid CT scanning systems, such as those that employ C-arms.

SUMMARY OF THE INVENTION

The foregoing are among the objects attained by the invention which provides, in some aspects, improved methods and apparatus for digital data processing and, more particularly, computed tomography volume reconstruction, e.g., by backprojection. These can be implemented, by way of non-limiting example, on commodity central processing units and graphics processors.

In one such aspect, the invention provides such methods and apparatus for use with C-arm and other CT systems, e.g., with non-rigid geometries. In such systems, by way of example, calibration can be performed to determine the exact position of the x-ray source and the exact orientation of the detector where each projection measurement is made. Next, a weighting coefficient can be determined for the voxels in each plane of a reconstruction volume at every possible projection. Finally, the order in which to process the voxels during image reconstruction can be determined. Following an actual CT scan procedure in which scans are obtained of a volume to be constructed, a system according to these and related aspects of the invention can use an optimal, pre-calculated processing method, while utilizing offsets and weighting coefficients determined during calibration, for performing backprojection image reconstruction.

Related aspects of the invention provide such methods and apparatus in which one or more of the foregoing computations are executed on a commodity graphical processing unit (GPU) (or other coprocessor) and/or central processing unit.

Still other aspects of the invention provide methods and apparatus as described above in which pre-calculation of mathematical corrections for geometric distortion of non-rigid CT systems, such as those employing C-arms, is performed by execution of one or more of the following steps: (i) calculating central axis of rotation; (ii) defining a coordinate system of reconstruction volume; (iii) calculating a resampled detector plane; (iv) defining source-normal-ray, and/or (v) calculating and storing offset.

Yet still other aspects of the invention provide methods and apparatus as described above in which pre-calculation of a weighting coefficient for projection voxels is performed by execution of one or more of the following steps: (i) moving to a projection position, e.g., by aligning the radiation source and detector at a given projection position; (ii) calculating S-offset value; (iii) building linear array of w values for 'S'; (iv) storing w values; and (v) looping back to perform these steps for another projection.

Yet other aspects of the invention provide such methods and apparatus in which pre-calculation for determining the optimal order in which to process individual voxels for backprojection reconstruction is performed by executing one or more steps which can include (i) defining brick size, (ii) defining projection sets, (iii) building a table of u-axis and v-axis coordinates at which each brick in reconstruction volume of interest will be projected onto resampled detector plane, (iv) defining an order to process bricks, e.g., based on each brick's proximity to one another when projected on resampled detector plane, (v) defining an order to process voxels, including selecting a primary axis to occupy consecutive locations in memory of digital data processor, and (vi) determining whether there are further bricks to process.

Still yet other aspects of the invention provide such methods and apparatus in which backprojection reconstruction is performed by executing one or more steps which can include (i) choosing a slab (e.g., a plane of bricks) to process, (ii) choosing a set of projections over which calculations will be performed (as determined, for example, during a prior pre-calculation stage), (iii) loading data from projection images, (iv) performing geometric normalization of a current slab, (v) performing one-dimensional pre-correction for Feldkamp backprojection of the current slab of data, (vi) choosing a brick in the current slab of reconstruction volume of interest to process (e.g., with u-axis and v-axis projection coordinates ordered as determined in during a prior pre-calculation stage), (vii) choosing x- and y-coordinates to process (e.g., with coordinate ordering determined in during a prior pre-calculation stage), (xii) determining a weighting coefficient (e.g., in accord with a prior pre-calculation stage), (xiii) choosing a z-coordinates of voxels in a current brick to process (e.g., in accord with an ordering determined during prior pre-calculation stage), and (ix) calculating intensity value of each voxel along the current z-coordinate for the selected x- and y-coordinates of the current brick.

Still other aspects of the invention provide methods and apparatus as described above that take advantage of recognition that perspective projection of a linear vector in the volume to the projection data is nearly linear over short sections of the volume and as such a linear interpolation is an acceptable approximation. By decomposing the reconstruction volume into a set of small bricks, systems and methods according to the invention can reduce the number of projection calculations by a factor that is equal to the number of voxels in a brick. This allows the address generation of the individual source data pixels to be performed by the vertex shaders of a GPU. This technique also allows the GPU's iterators to calculate the resampling coordinates and this further allows our implementation to employ the bilinear resampling hardware that is built into the GPU pipeline. In this way the projection data can be accessed as a simple independent (rather than dependent) read of the GPU's texture memory.

Methods and systems according to the invention have numerous advantages, among which are that they can perform acquisition and reconstruction in real-time, such as a system that produces a continuous stream of two- or three-dimensional reconstructions of an object. One application for such systems and methods are for physicians performing image guided surgery.

Such systems and methods also decrease the time it takes for a computer system to perform backprojection, and other image reconstruction methods, for computed tomography. Furthermore, they permit this to be done cost-effectively, e.g., without specialized CT hardware.

Moreover, such systems provide for determining the effect that a non-circular orbit has on C-arm and other image acquisition equipment, thereby allowing the volume reconstruction data processor to compensate for such effects and, furthermore, to transfer such projection sets into a usable form for backprojection (e.g., by the Feldkamp technique).

Yet still other aspects of the invention provide a computerized tomography (CT) system which includes an image acquisition apparatus, which further includes a C-arm, a radiation source, a detector, a patient or subject of interest, and a reconstruction volume of interest; a plurality of projection images; and a digital data processor, which further includes a random access memory (RAM), an input/output (I/O) channel, a central processing unit (CPU), a graphics processing unit (GPU), and a personal computer (PC) bus. The GPU further includes a personal computer (PC) bus interface, a GPU bus, a GPU RAM, a geometric mapping section, which further includes a plurality of vertex shaders, and a pixel processing section, which further includes a render target direct memory access (DMA) engine, a plurality of filters, and a plurality of pixel shaders.

Still yet other aspects of the invention provide methods for operation of the foregoing and other CT systems including the steps of pre-calculating a transform to normalize geometry, pre-calculating a matrix of weight coefficients, pre-calculating an optimal brick order, acquiring projection image data, and performing backprojection.

Yet still other aspects of the invention provide a CT system as described above for performing geometric calibration which includes a plurality of detector image points, a plurality of resampled detector planes, a plurality of resampled center points, a resampled circle, a z-axis, a u-axis, a v-axis, a x-axis, a y-axis, a β angle, an S offset, a T offset, a source normal ray, and an ($f_u$, $f_v$) intercept.

A method of performing geometric calibration on such and other CT system can include the steps of calculating a central axis of rotation, defining a coordinate system of the reconstruction volume, calculating a resampled detector plane, defining a projection-normal, and calculating and storing a matrix of S and T offsets and their corresponding weighting coefficient "w".

According to still further aspects of the invention, a CT system as described above can include means for calculating a weighting coefficient, which means includes a source-to-image distance (SID), a source-to-object distance (SOD), an $f_s$ calculation, and an r calculation, and a plane with a constant SOD/SID ratio. A method of calculating a weighting coefficient includes the steps of moving to a projection position, calculating a w value, building a linear array of w values for 'S', storing w values, and repeating for additional projections.

In still further aspects of the invention, a CT system as described above can include means for pre-calculating the optimal order in which to process individual voxels includes a plurality of bricks, each of which contain a plurality of voxels, and a resampled detector plane, which further includes a plurality of brick shadows. A method of pre-calculating the optimal order in which to process individual voxels can include the steps of defining the brick size, defining the projection sets, building a u/v table for all bricks, defining the order in which to process bricks, defining the order in which to process voxels, and repeating for additional bricks.

Yet still other aspects of the invention provides systems and methods as described above in which the performance of backprojection image reconstruction includes the steps of choosing a slab, choosing a projection set, loading data, performing geometric normalization, performing one-dimensional pre-correction, choosing a brick, choosing an X-coordinate, choosing a Y-coordinate, determining a weight coefficient, choosing a Z-coordinate, calculating an intensity value, determining whether to repeat for voxels along the z-axis, determining whether to repeat for voxels along the y-axis, determining whether to repeat for voxels along the x-axis, determining whether to repeat for other bricks, determining whether to repeat for other projection sets, and determining whether to repeat for other slabs.

DETAILED DESCRIPTION OF THE ILLUSTRATED EMBODIMENT

The present invention is a system for and method of reconstructing CT volumes by use of backprojection on commodity central processing units and graphics processors. The CT system periodically performs pre-calculations and stores the resulting information. First, for systems with non-rigid geometries, calibration is performed to determine the exact position of the x-ray source and the exact orientation of the detector, where each projection measurement is made. Next, a weighting coefficient is determined for every voxel in each plane of a reconstruction volume for every possible projection. Finally, the order in which to process each voxel during image reconstruction is determined. Following an actual CT scan procedure, the computer system of the present invention uses the optimal, pre-calculated processing method, while utilizing offsets and weighting coefficients, for performing backprojection image reconstruction.

Figure 1A:
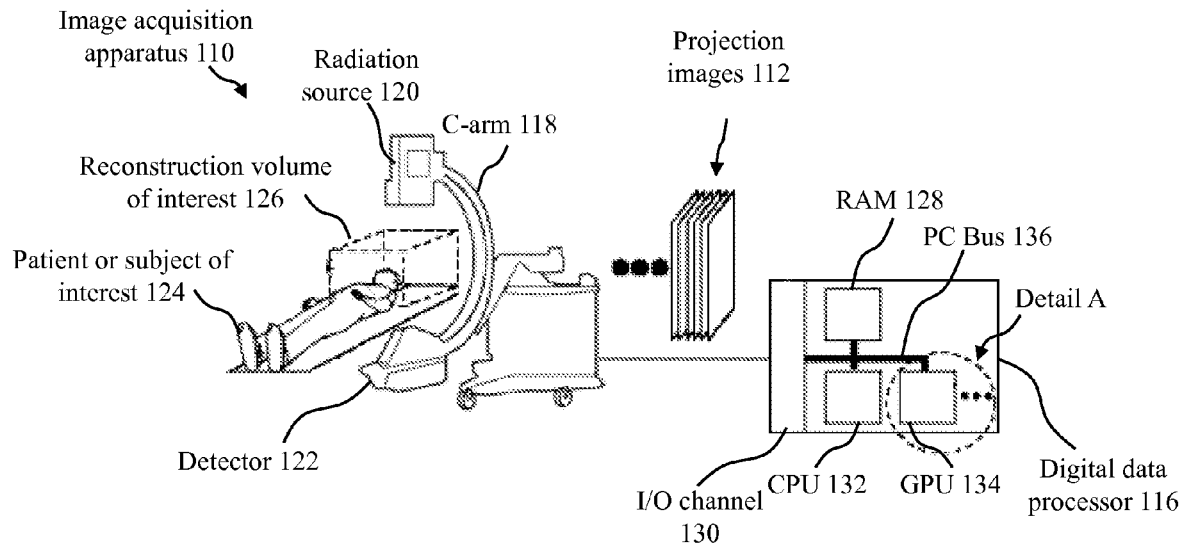
FIG. 1A illustrate a computerized tomography (CT) system in accordance with one practice of the invention.
Figure 1B:
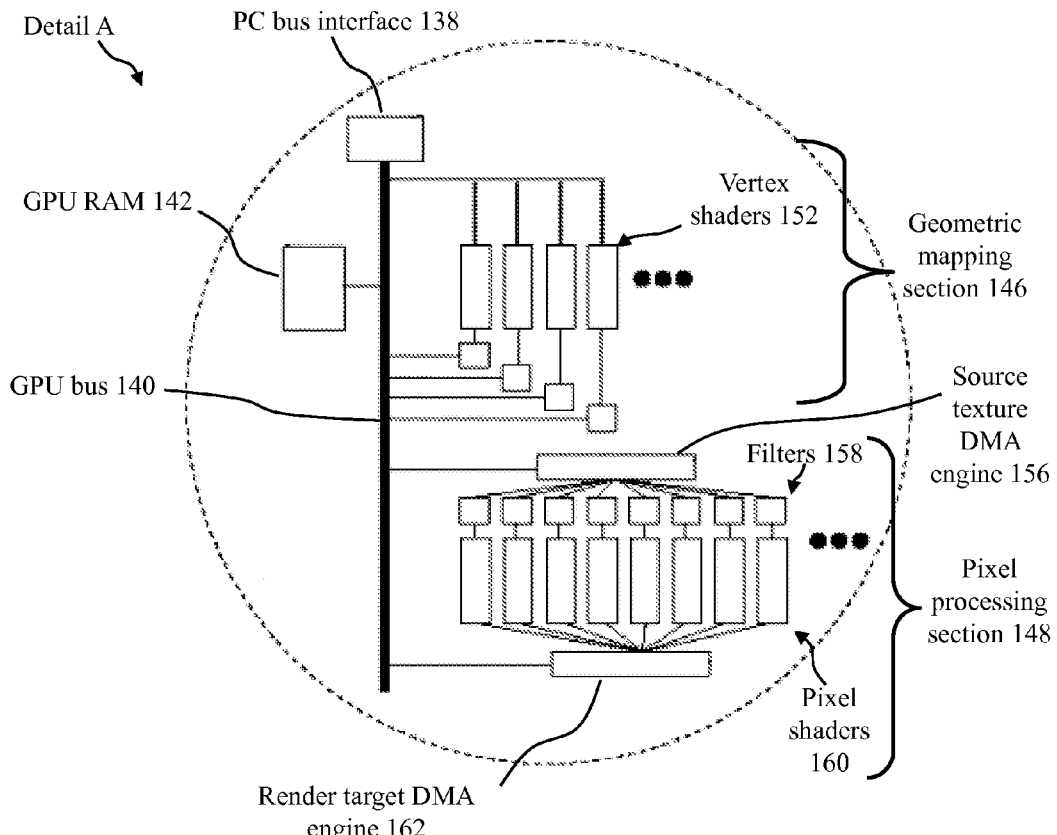
FIG. 1B illustrates a preferred architecture of a computerized tomography (CT) system in accordance with one practice of the invention.

FIGS. 1A and 1B illustrate a computerized tomography (CT) system 100 in accordance with the invention. CT system 100 includes an image acquisition apparatus 110, an unspecified plurality of projection images 112, and a digital data processor 116. Image acquisition apparatus 110 further includes a c-arm 118, a radiation source 120, a detector 122, a patient or subject of interest 124, and a reconstruction volume of interest 126. Digital data processor 116 further includes a random access memory (RAM) 128, an input/output (I/O) channel 130, a central processing unit (CPU) 132, a graphical processing unit (GPU) 134, and a personal computer (PC) bus 136. A typical GPU 134 is shown in more detail in reference to FIG. 1B as Detail A. GPU 134 includes a PC bus interface 138, a GPU bus 140, a GPU RAM 142, a geometric mapping section 146, and a pixel processing section 148. Geometric mapping section 146 further includes an unspecified plurality of vertex shaders 152. Pixel processing section 148 further includes a source texture direct memory access (DMA) engine 156, an unspecified plurality of filters 158, an unspecified plurality of pixel shaders 160, and a render target DMA engine 162.

FIG. 1A illustrates one specific architecture of CT system 100. However, those skilled in the art will appreciate that similar architectures could also be employed that realize the innovations set forth by the invention. Image acquisition apparatus 110 represents a conventional CT system, such as a CT scan machine, used for capturing radiation transmission information passed from radiation source 120 through patient or subject of interest 124 to detector 122. An x-ray is representative of one specific class of radiation transmission in which radiation source 120 is an x-ray source and detector 122 is an x-ray detector; it is understood that other classes of radiation may be used in this invention. Radiation source 120 and detector 122 are attached to a C-arm 118. C-arm 118 is a support that is designed to rotate radiation source 120 and detector 122 around patient or subject of interest 124 in an orbit that is as close as possible to a circle. With respect to the structure of image acquisition apparatus 110, FIG. 1A illustrates a C-arm CT scanner, in that radiation source 120 and detector 122 are attached to a C-arm 118. However, those skilled in the art will appreciate that traditional, toroidal-shaped CT scan machines, in which radiation source 120 and detector 122 move on a fixed geometry, may also be employed to realize the invention. Patient or subject of interest 124 represents the object to be imaged by image acquisition apparatus 110. This is illustrated as a human patient in FIG. 1A, but it is understood that the invention has applicability to a variety of other industries and, thus, patient or subject of interest 124 is representative of any object to image for computerized tomography. Reconstruction volume of interest 126 is the specific area of patient or subject of interest 124 to be imaged and reconstructed. With respect to FIG. 1A, note that while the patient's head is the true subject of interest, reconstruction volume of interest 126 is a larger area representative of the total area to be imaged, which encompasses the head. Projection images 112 represent a collection of two-dimensional images that result from the projection of radiation from radiation source 120 through reconstruction volume of interest 126 to detector 122 at multiple angles. In the case in which x-ray is used as the radiation source, projection images 112 represent a collection of x-ray images.

Digital data processor 116 represents a conventional workstation, personal computer, server, or other computing device, as is well-known in the art, which is responsible for controlling image acquisition apparatus 110, capturing and storing projection images 112, and performing image reconstruction. Digital data processor 116 contains conventional input/output channel 130, which is used for communicating with image acquisition apparatus 110. RAM 128 represents conventional memory used by the common processes of digital data processor 116, whereas other memory used specifically for image processing will be described in reference to FIG. 1B. CPU 132 is a conventional, general purpose processor unit that is also well-known in the art. GPU 134 is coupled with and provides assistance to CPU 132 as a coprocessor. It is also understood that digital data processor 116 may contain one or more GPUs 134. GPU 134 represents a conventional graphics processor, such as those offered by ATI or NVidia, which is used specifically for performing computation-intensive graphic functions and, thus, lightens the processing load of CPU 132. The specific architectural components of GPU 134 are described in more detail with reference to FIG. 1B. All components within digital data processor 116 communicate via conventional PC bus 136. PC bus 136 is a group of connections or circuits over which multiple computing elements of digital processor 116 communicate with one another.

FIG. 1B illustrates a typical architecture of GPU 134, as described below. However, those skilled in the art will appreciate that similar GPU architectures that realize the innovations set forth by the invention could also be employed. PC bus interface 138 represents an interface by which components of GPU 134 communicate with PC bus 136 via GPU bus 140. GPU RAM 142 provides memory functions specific to GPU 134 and interfaces with RAM 128 of digital data processor 116.

Additional components of GPU 134 are divided into geometric mapping section 146 and pixel processing section 148. Geometric mapping section 146 is responsible for mapping the three-dimensional geometry of reconstruction volume of interest 126 to the two-dimensional geometry of a plurality of projection images 112 during processing calculations, such as image reconstruction. A plurality of vertex shaders 152, alternately known in the art as vertex processors, manipulate three-dimensional vertex data values of reconstruction volume of interest 126, or smaller, sub-elements of reconstruction volume of interest 126, to be described in detail as "bricks" in reference to FIGS. 8A and 8B. Vertex shaders 152 are graphical processing functions of graphical processing units, such as GPU 134, that change the vertex values of graphical data, data such as color, textures, or positions in space. It is understood that, because vertex shaders 152 operate as n-way single instruction multiple data (SIMD) processors, additional processors that have greater or lesser processing speeds may be used to realize the invention, especially in future implementations of GPU 134.

Source texture DMA engine 156 allows the transfer of data from one memory area of digital data processor 116 to pixel shaders 160 via GPU bus 140, without the need to go through CPU 132. A plurality of filters 158, one for each pixel shader 160, provide interpolation and other filtering functions on projection images 112 during processing calculations, such as image reconstruction. Pixel shaders 160, alternately known in the art as pixel processors, are data processing agents imbedded within graphical processing units, such as GPU 134, that change the pixel values of graphical data. Pixel shaders 160 are responsible for calculating the values of voxels of a portion of projection images 112. The operation of pixel shaders 160 are such that data is distributed into pixel shaders on a pixel-by-pixel or voxel-by-voxel basis, and they work on consecutive pixels or voxels in a volume such as a reconstruction volume of interest 126. Additional optimization techniques for processing pixels and/or voxels are presented in more detail in reference to FIGS. 8A, 8B, and 9. While a plurality of eight pixel shaders 160 is shown, it is understood that additional processors that have greater or lesser processing speeds may be used to realize the invention, especially in future implementations of GPU 134. Render target DMA engine 162 provides an additional direct memory engine for transferring data from pixel shaders 160 back to GPU memory, such as GPU RAM 142, without the need to go through CPU 132.

In operation, image acquisition apparatus 110 generates a plurality of projection images 112 by projecting radiation from radiation source 120 through patient or subject of interest 124 and reconstruction volume of interest 126 to detector 122 at a number of different angles, or projection positions. The various projection positions of radiation source 120 and detector 122, with respect to reconstruction volume of interest 126, are achieved through the mechanical rotation performed by a C-arm 118. Projection images 112 are collected by CPU 132 of digital data processor 116 and are stored in either short-term RAM 128 or written to long-term storage (not shown). Digital data processor 116 performs image reconstruction by transferring projection images 112 data from RAM 128 to GPU 134. Vertex shaders 152 map three-dimensional geometric information of the projection data, while pixel shaders 160 perform read and write and arithmetic functions that change pixel and/or voxel values of the reconstruction volume and projection images 112 data.

Figure 2:
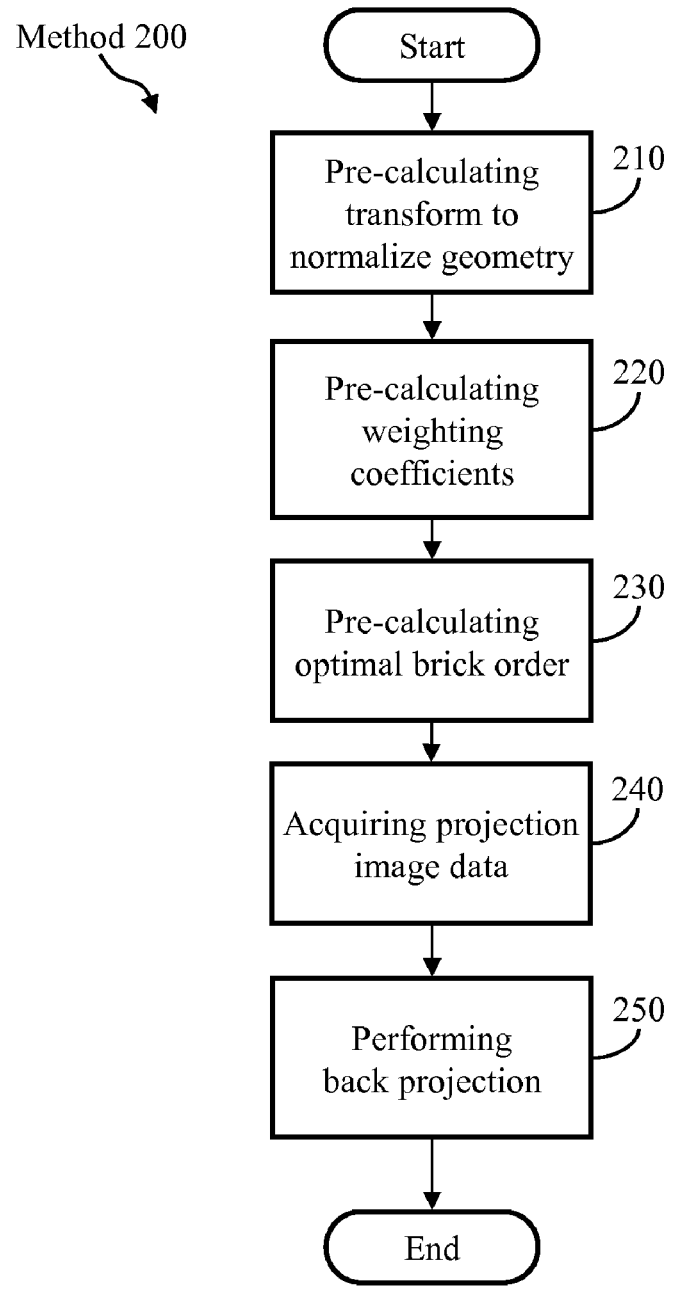
FIG. 2 illustrates a high-level method of performing CT volume reconstruction according to one practice of the invention.

FIG. 2 illustrates a high-level method 200 of performing CT volume backprojection reconstruction.

Step 210: Pre-Calculating Transform to Normalize Geometry

In this step, for non-rigid C-arm based CT systems, prior to an actual CT scan procedure, digital data processor 116 pre-calculates a transform to normalize the geometry of the non-circular orbit of image acquisition apparatus 110. The preferred implementation of this step involves imaging a calibration phantom at various projection positions to compare the projected results of targets within the phantom to the expected results. This process is described in complete detail in reference to Method 500. Method 200 proceeds to step 220.

Step 220: Pre-Calculating Weighting Coefficients

In this step, digital data processor 116 pre-calculates a weighting coefficient for each voxel in reconstruction volume of interest 126 for each projection position. This weighting accounts for the positioning of material throughout the volume, as positioning impacts the amount of radiation absorbed and the projection shadow cast on detector 122. Because reconstruction volume of interest 126 encompasses patient or subject of interest 124 during an actual CT scan procedure, each weighting coefficient can be calculated prior to the actual procedure. The preferred implementation of this step involves calculating a weighting coefficient as a function of the distance from radiation source 120 to reconstruction volume of interest 126, the angle of the projection position, and if necessary, the transform to normalize the geometry of non-rigid CT scanning systems as described in Step 210. This method requires calculating only a single plane of weighting coefficients per projection, rather than an entire volume of weighting coefficients and will be described in complete detail in reference to Method 700. Method 200 proceeds to step 230.

Step 230: Pre-Calculating Optimal Brick Order

In this step, digital data processor 116 pre-calculates the optimal order in which GPU 134 should process projection images 112 of reconstruction volume of interest 126 during a reconstruction process. The preferred implementation of this step involves dividing reconstruction volume of interest 126 into sections known as "bricks," and processing bricks sequentially, based on the proximity of each brick's image data on projection image 112. Furthermore, the optimal order in which GPU 134 processes individual voxels of each brick is calculated. This process is described in complete detail in reference to Method 900. Method 200 proceeds to step 240.

Step 240: Acquiring Projection Image Data

In this step, digital data processor 116 acquires and stores projection images 112 data, as image acquisition apparatus 110 performs a CT scan process on patient or subject of interest 124 across each projection position. Method 200 proceeds to step 250.

Step 250: Performing Backprojection

In this step, digital data processor 116 performs backprojection to reconstruct a three-dimensional representation of reconstruction volume of interest 126. The preferred implementation of this step involves dividing reconstruction volume of interest 126 into cross-sections known as "slabs," and processing voxels on a brick-by-brick basis for each slab across a set of projection images 112, using the optimal order to process both bricks and voxels as described in Step 230. Results of pre-calculation steps 210, 220, and 230 are further used in step 250. This process is described in complete detail in reference to Method 1000. Method 200 ends.

Figure 3A:
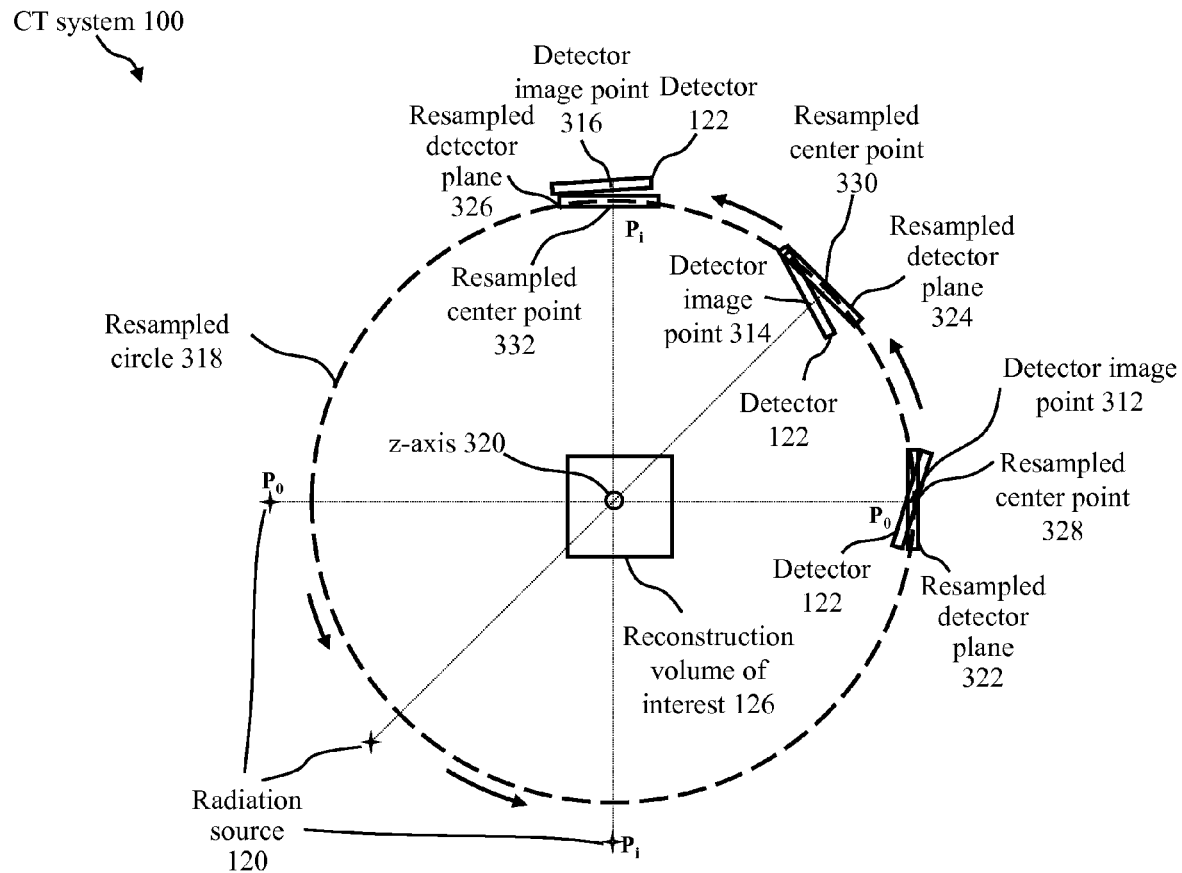
FIG. 3A illustrates a top-level view of a CT system in accordance with one practice of the invention.
Figure 3B:
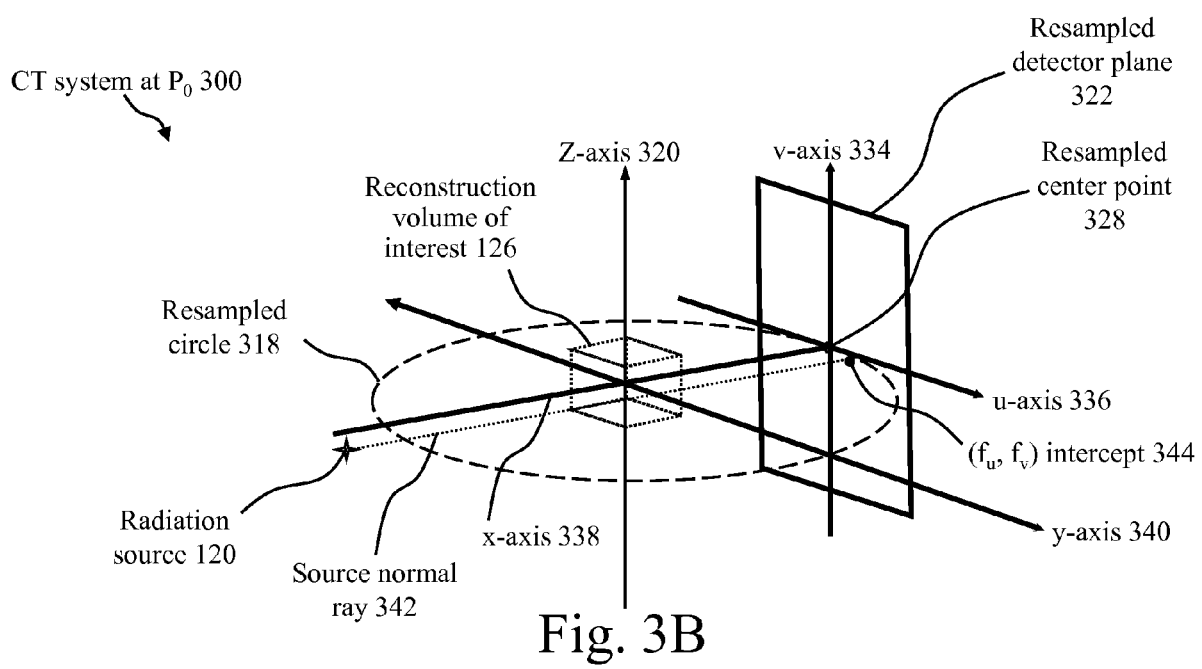
FIG. 3B illustrates a side-level view of a CT system in accordance with one practice of the invention.
Figure 4:
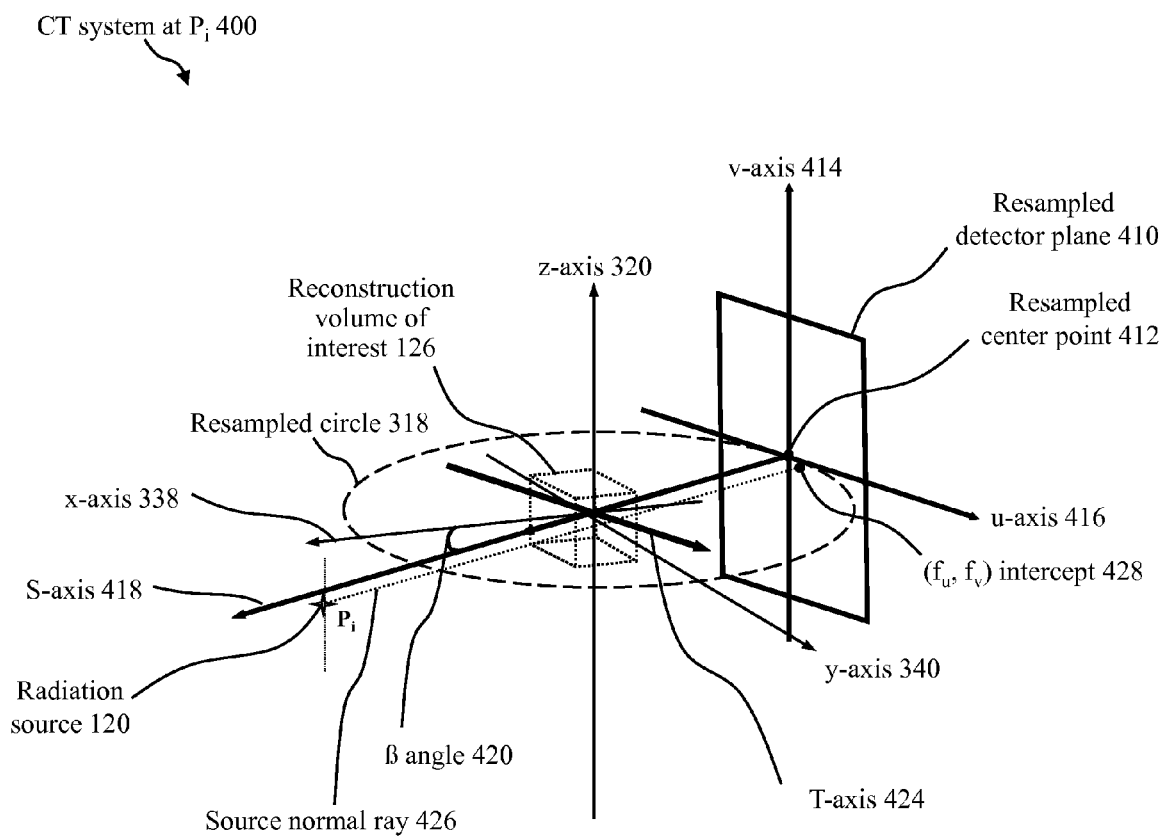
FIG. 4 illustrates an alternate side-level view of a CT system in accordance with one practice of the invention.
Figure 5:
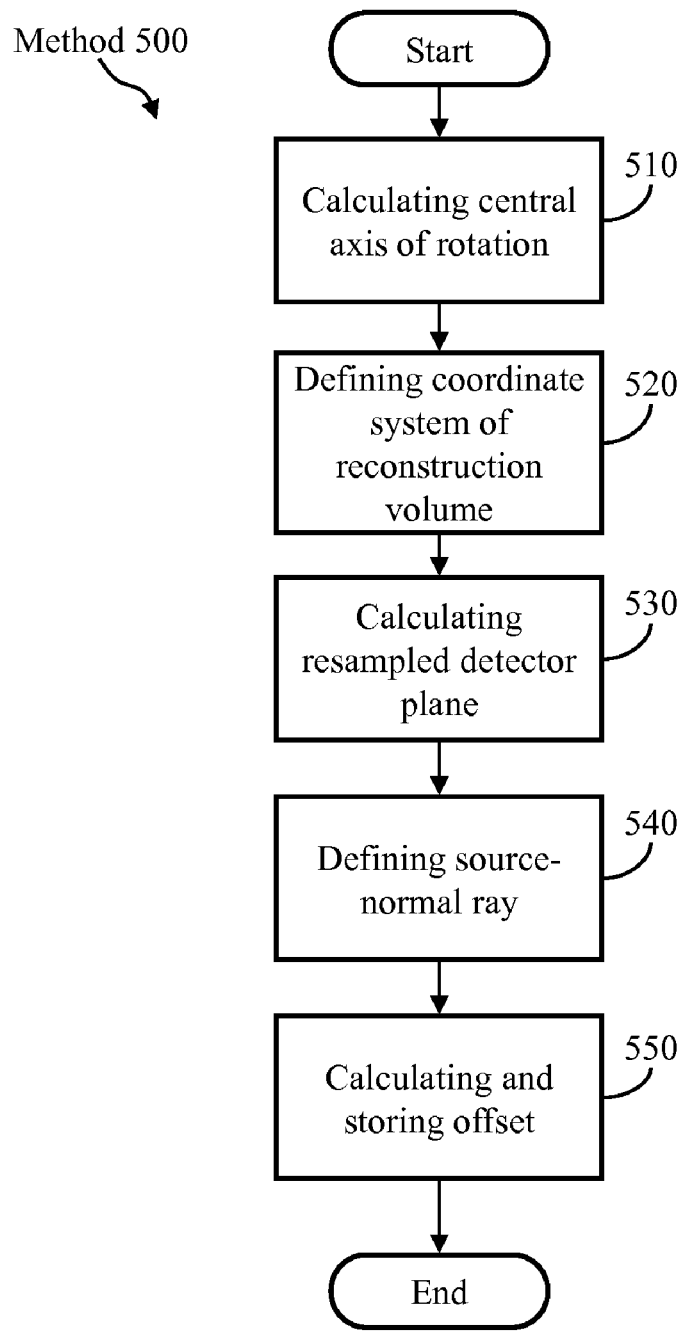
FIG. 5 illustrates a method of performing geometric calibration of a non-rigid C-arm based CT system in accordance with one practice of the invention.

FIGS. 3A, 3B, and 4 illustrate system-level diagrams for, and FIG. 5 illustrates a specific method of, pre-calculating mathematical corrections for geometric distortion of non-rigid CT systems, such as those employing a C-arm, as previously described in reference to Step 210 of Method 200.

FIG. 3A illustrates a view along the axis of rotation of CT system 100 that includes a detector image point 312 (in projection $P_0$), a detector image point 314 (in a subsequent projection $P_n$), a detector image point 316 (in a subsequent projection $P_i$), a resampled circle 318, a z-axis 320, a resampled detector plane 322, a resampled detector plane 324, a resampled detector plane 326, a resampled center point 328, a resampled center point 330, and a resampled center point 332.

FIG. 3B illustrates CT system 100 at $P_0$ 300 at a oblique view that includes a v-axis 334, a u-axis 336, an x-axis 338, a y-axis 340, a source normal ray 342, and the normal ray's ($f_u$, $f_v$) intercept 344 with the resampled detector plane 322.

Many CT systems utilize a C-arm or other non-rigid structure, in which the position of radiation source 120 and detector 122 are subject to aforementioned geometric distortions. While there may be numerous methods that compensate for such distortion, the following describes the preferred embodiment of the invention. FIG. 3A illustrates CT system 100 at three different projection positions during a system calibration process. System calibration is performed as preparation for operation in a specific orientation. This is done before the actual imaging process begins. A conventional calibration object, alternatively known as a "calibration phantom" in the art, is placed in the position in which a real patient or subject of interest 124 would be imaged. Typically, the calibration scan replicates the number of projection positions used during the system's intended operation. Each projection position, and the resulting projection image 112, is denoted as $P_i$, where $P_0$ indicates the first projection position and $P_n$ indicates the last. A calibration phantom is an object of simple geometry, such as a cube or sphere, designed to allow for the assessment of volumetric measurement accuracy. With respect to FIG. 3A, the calibration phantom is illustrated as reconstruction volume of interest 126. The calibration phantom contains a number of high-density targets whose true geometry is known. While six targets will suffice to compensate for a detector that moves with six degrees of freedom, in the preferred embodiment of the invention, a calibration phantom with eight or more targets is assumed. The expected target locations can be compared to the actual projected targets and a mathematical table of projection offsets can be calculated.

Note that at $P_0$, detector 122 is not tangential to a true circular orbit that passes through detector 122 at the other two projection positions. Additionally, note that the ray extending from radiation source 120 to detector 122 passes through reconstruction volume of interest 126, but not the exact center of the volume. Although these positions are perhaps exaggerated for illustrative purposes, they are representative of some of the common geometric distortions that occur in which radiation source 120 and/or detector 122 wobbles during projection acquisition and therefore, a slightly different projection image is acquired from that which was expected.

By comparing the expected target locations of a calibration phantom with the actual projected targets, the true location of detector 122 can be determined with respect to its six degrees of freedom and thus, a detector image point can also be determined. With respect to FIG. 3A, this is illustrated as detector image point 312 at projection position $P_0$. A true circle, illustrated as resampled circle 318, can be fit to these points to minimize the root mean square (RMS) error of the collective detector image points. Resampled circle 318 is further illustrated from a side perspective in FIG. 3B. The coordinate system of resampled circle 318 is, therefore, established. The central axis of rotation of resampled circle 318 passes through its center point and is illustrated as z-axis 320. X-axis 338 and y-axis 340 form a plane perpendicular to z-axis 320 and parallel to the plane of resampled circle 318, as illustrated in FIG. 3B. It is important to note that both x-axis 338 and y-axis 340 remain fixed, relative to reconstruction volume of interest 126 at the original projection position $P_0$.

With respect to FIG. 3A, note that at each projection position, detector 122 is not tangential to resampled circle 318. Therefore, a new plane must be established that is tangential to resampled circle 318 at each projection position. This plane is represented as a resampled detector plane and is illustrated in FIG. 3B as resampled detector plane 322 at projection $P_0$. The coordinate system of each resampled detector plane can then be established as illustrated in FIG. 3B. U-axis 336 is perpendicular to z-axis 320 and is parallel to a tangent of resampled circle 318. V-axis 334 is parallel to z-axis 320 and passes through the point of tangency at resampled circle 318. It is important to note that both v-axis 334 and u-axis 336 are relative to the resampled detector plane at each projection position. The intersection of u-axis 336 and v-axis 334 at each projection is the resampled center point, and is illustrated in FIG. 3B as resampled center point 328. Note that the ray originating at radiation source 120 and extending through reconstruction volume of interest 126 is parallel to x-axis 338, but does not, typically, intersect v-axis 334 or u-axis 336. This ray, illustrated as source normal ray 342, passes through resampled detector plane 322 at some offset from v-axis 334 and u-axis 336; FIG. 3B illustrates this as $(f_u, f_v)$ intercept 344.

FIG. 4 illustrates CT system 100 at $P_i$ 400 at a side-level view that includes a resampled detector plane 410, a resampled center point 412, a v-axis 414, a u-axis 416, a S-axis 418, a β angle 420, a T-axis 424, a source normal ray 426, and a $(f_u, f_v)$ intercept 428.

FIG. 4 is illustrated at the same perspective as CT system 100 of FIG. 3B, in that radiation source 120 and resampled detector plane 410 were both moved from $P_0$ to $P_i$, and the viewer's perspective also rotated to maintain the same view relative to the radiation source and the detector plane. Note that reconstruction volume of interest 126, x-axis 338, and y-axis 340 remain fixed to original position $P_0$, but appear to have rotated to the left, as the viewer's perspective rotated to the right. The plane that lies on the same plane as resampled circle 318, passes through the center point of resampled circle 318, and intersects the resampled center point of the respective detector plane at each position $P_i$ is the S-axis 418. With respect to FIG. 4, S-axis 418 intersects resampled center point 412 of resampled detector plane 410. S-axis offset of the radiation source 418 describes the distance between the resampled detector plane and radiation source at each projection position. This is illustrated as the length from resampled center point 412 to a plane that extends through radiation source 120 along source normal ray 426 in FIG. 4. With respect to FIG. 3B at position $P_0$, note that S-axis 418 is aligned with x-axis 338. However, with respect to FIG. 4 at position $P_i$, the difference between S-axis 418 and x-axis 338 is illustrated as angle β 420, this allows the system to calculate the angle between the current projection position $P_i$ and the original projection position $P_0$. Additionally, the position of any voxel in reconstruction volume of interest 126 at any projection position $P_i$ can be established as a function of β angle 420 and its (x, y) coordinates, with respect to its original projection position $P_0$. This position can be converted to an S offset and T offset, with S axis 422 always parallel to the source normal ray 418 and T-axis always aligned parallel with u-axis 416 with respect to the current projection position.

FIG. 5 illustrates a method 500 of pre-calculating mathematical corrections for geometric distortion of non-rigid CT systems, such as those employing C-arms. FIGS. 3A, 3B, and 4 are referenced throughout.

Step 510: Calculating Central Axis of Rotation

In this step, digital data processor 116 calculates the optimal central axis of rotation. While there are numerous models for performing this calculation, the preferred method is described here. For each calibration projection, as defined by $P_i$, radiation source 120 and detector 122 are positioned to their respective locations around a calibration phantom, shown as reconstruction volume of interest 126. Radiation source 120 projects x-ray energy towards reconstruction volume of interest 126. Those photons not absorbed in reconstruction volume of interest 126 are transmitted toward, and impact on, detector 122. Digital data processor 116 compares the expected target locations of reconstruction volume of interest 126, which are known a priori and stored in long-term memory (not shown) of digital data processor 116, with the actual projected targets acquired. Once all target locations are compared and detector image points are calculated and stored for all projection positions, digital data processor 116 uses a conventional mathematical algorithm, such as the Gauss-Newton method for finding the Least Mean Square fit, to calculate a best-fit circle that minimizes the RMS of all detector image points. This best-fit circle is illustrated as resampled circle 318. The plane that runs perpendicular to resampled circle 318 and extends through its center point is calculated as the central axis of rotation, shown as z-axis 320. While there are other methods for calculating the central axis of rotation, each method will always define a resampled circle and z-axis. Method 500 proceeds to step 520.

Step 520: Defining Coordinate System of Reconstruction Volume

In this step, digital data processor 116 calculates and stores the coordinate system of reconstruction volume of interest 126. With respect to FIG. 3B, x-axis 338 is calculated as the plane that is aligned with resampled circle 318 and intersects the mid-point of resampled circle 318. Y-axis 340 is calculated as the plane that is aligned with resampled circle 318 and passes through the mid-point of reconstruction circle 318. Both x-axis 338 and y-axis 340 remain fixed, with respect to the original position $P_0$ of reconstruction volume of interest 126. Method 500 proceeds to step 530.

Step 530: Calculating Resampled Detector Plane

In this step, for each projection position $P_i$, digital data processor 116 calculates and stores a resampled detector plane that is tangential to resampled circle 318. This calculation is performed by comparing the actual projected targets of reconstruction volume of interest 126 with the expected targets, and then aligning detector 122 with resampled circle 318. FIG. 3A illustrates three different examples of actual detector positions and their respective positions after resampling is performed. Method 500 proceeds to step 540.

Step 540: Defining Source-Normal-Ray

In this step, for each projection position $P_i$, digital data processor 116 calculates and stores source-normal-ray 426, which is calculated as the line that lies in the same plane as resampled circle 318 and which passes through the center point of resampled circle 318 and intersects the resampled center point of the resampled detector plane, which is illustrated as resampled detector plane 410 in FIG. 4. Method 500 proceeds to step 550.

Step 550: Calculating and Storing Offset

In this step, for each projection position $P_i$, digital data processor 116 defines and calculates β angle 420 as the difference between x-axis 338 and S-axis 418. Using β angle 420; digital data processor 116 can also define and calculate the position of any voxel [x, y, z] in reconstruction volume of interest 126 for any projection position $P_i$. This position is a function of S offset 422 and T offset 424. S offset 422 is calculated as S=x cos β+y sin β. T offset 424 is calculated as T=−x sin β+y cos β. Method 500 ends.

While FIGS. 3A, 3B, 4, and 5 compensate for geometric distortion of non-rigid CT systems, the remaining aspects of the invention apply to any system in which backprojection is performed.

Figure 6A:
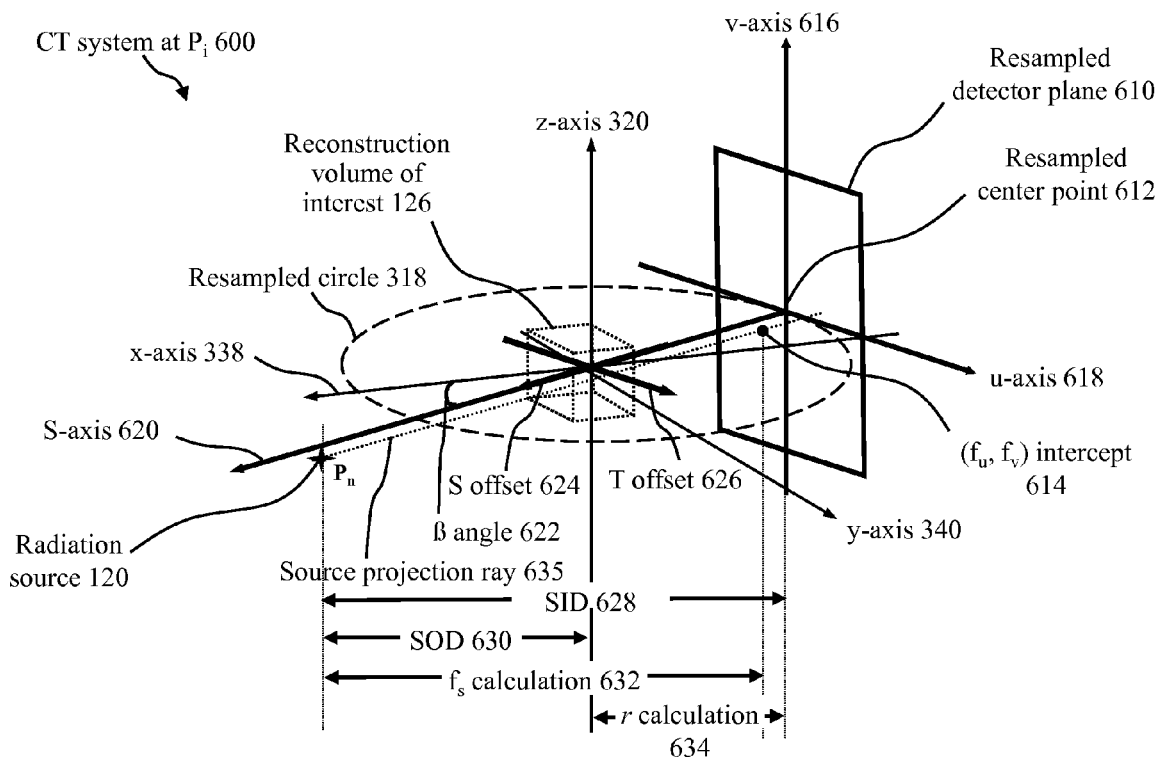
FIG. 6A illustrates an example projection position of a CT system in accordance with one practice of the invention.
Figure 6B:
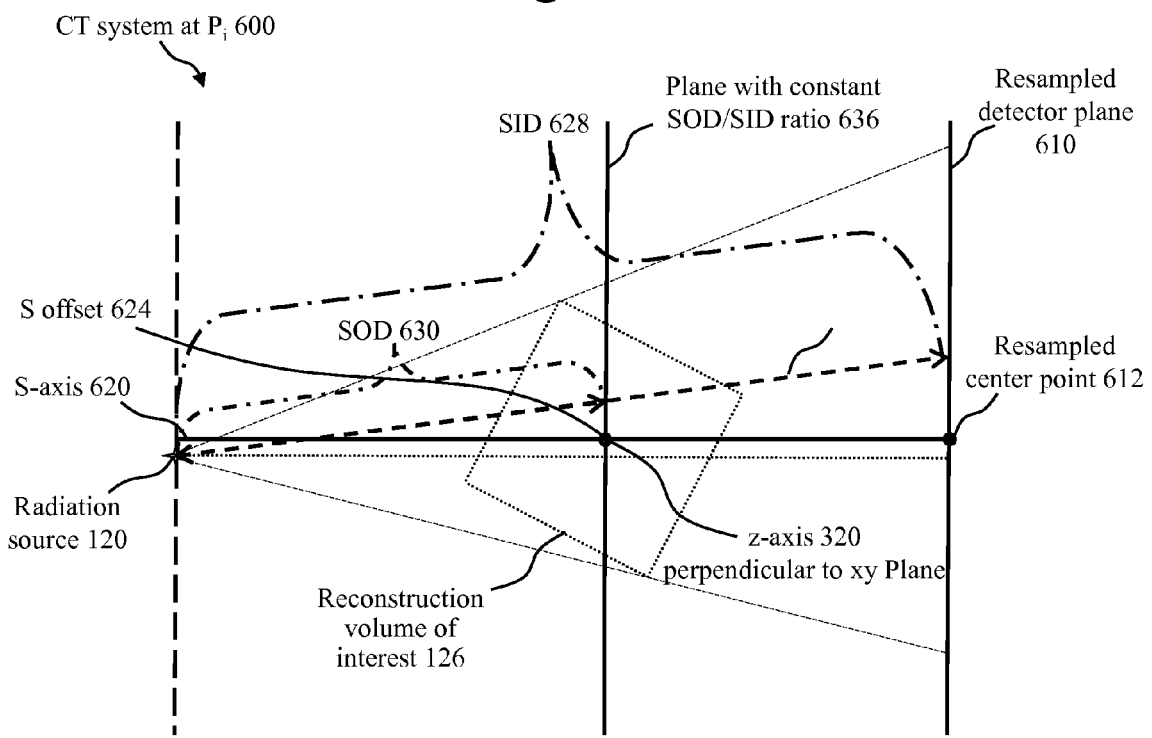
FIG. 6B illustrates a top-level view of an example projection position of a CT system in accordance with one practice of the invention.
Figure 7:
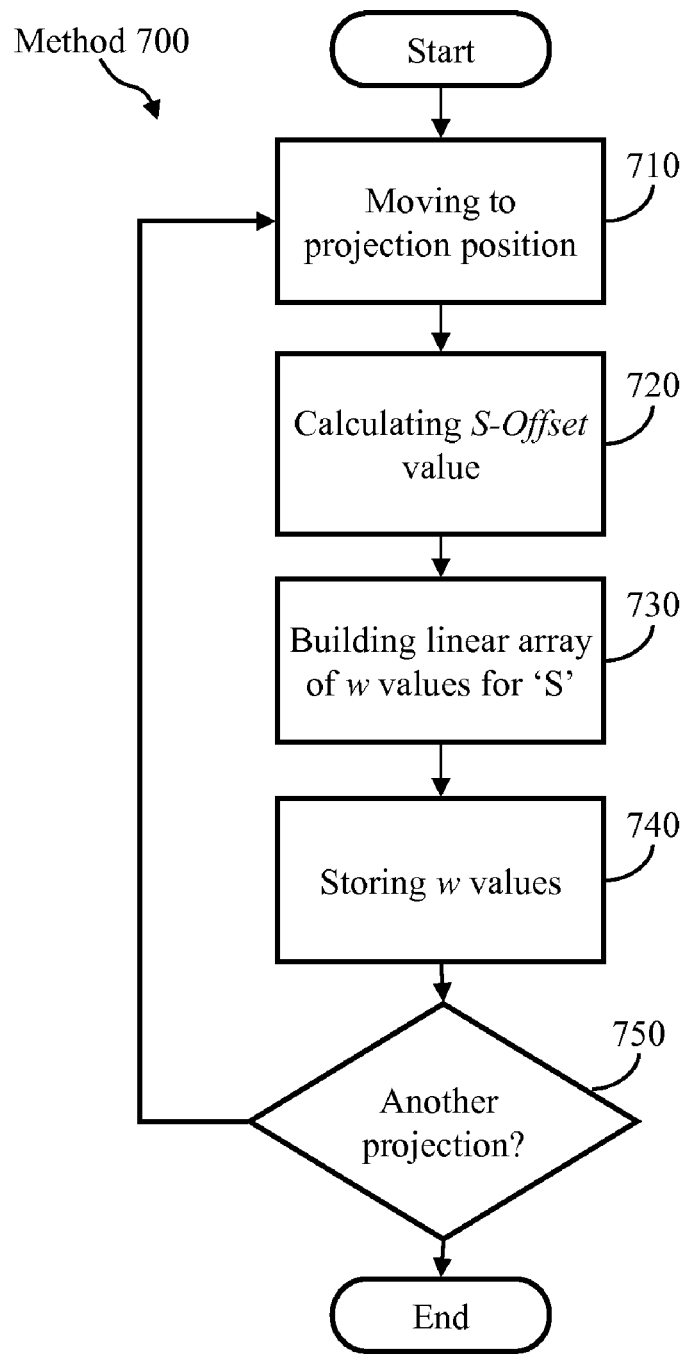
FIG. 7 illustrates a method of pre-calculating a weight coefficient for projection voxels in accordance with one practice of the invention.

FIGS. 6A and 6B illustrate system-level diagrams for, and FIG. 7 illustrates a specific method of, pre-calculating a weight coefficient for projection voxels, as previously described in reference to Step 220 of Method 200 of FIG. 2.

FIG. 6A illustrates CT system 100 at $P_i$ 600 and includes a resampled detector plane 610, a resampled center point 612, an $(f_u, f_v)$ intercept 614, a v-axis 616, a u-axis 618, a S-axis 620, a β angle 622, an S offset 624, a T offset 626, a source-to-image distance (SID) 628, a source-to-object distance (SOD) 630, an $f_s$ calculation 632, an r calculation 634, and a source projection ray 635.

FIG. 6B illustrates CT system 100 at $P_i$ 600 at a top-level view and includes a plane with constant SOD/SID ratio 636.

In reference to FIG. 6A, as radiation source 120 and detector 122 rotate around reconstruction volume of interest 126, the distance from any voxel in reconstruction volume of interest 126 to both radiation source 120 and resampled detector plane 610 varies. As a result, the shadow size cast onto resampled detector plane 610 correlates to the distance from radiation source 120 to reconstruction volume of interest 126 and from reconstruction volume of interest 126 to resampled detector plane 610. Therefore, a weighting coefficient must be calculated for each voxel in reconstruction volume of interest 126 and factored when backprojection calculations are performed. Because these weights are a function of the geometry of the system (and are not dependent on the actual projection data values), these weights can be calculated prior to an actual CT scan procedure and stored in digital data processor 116.

With reference to FIGS. 6A and 6B, the calculation of the weighting coefficient varies, depending on whether the orbit of image acquisition apparatus 110 is a circular or a non-circular trajectory. For circular trajectories, the weighting coefficient is a function of a source-to-object distance calculation, represented as SOD 630, and S offset 624. Mathematically, the weighting coefficient is represented as w=[SOD/(SOD−S)]$^2$. For non-circular trajectories, the ray originating at radiation source 120 and extending through reconstruction volume of interest 126, illustrated as source projection ray 635, intersects resampled detector plane 610 at some offset from resampled center point 612. This offset can occur along both u-axis 618 and v-axis 616 and, with respect to FIG. 6A, is illustrated as $(f_u, f_v)$ intercept 614. The $(f_u, f_v)$ intercept 614 describes the deviation of radiation source 120 from its normal trajectory, in terms of its projection of source normal ray 635 onto resampled detector plane 610. Thus, for non-circular trajectories, the weighting coefficient is also a factor of a SOD calculation and S offset 624. However, SOD is illustrated by calculating $f_s$ 632 minus r 634. Mathematically, this is represented as: SOD=$f_s$−r. $f_s$ 632 represents the distance from radiation source 120 to resampled detector plane 610, where source normal ray 635 intersects resampled detector plane 610 at $(f_u, f_v)$ intercept 614. The r calculation 634 represents the distance from z-axis 320 to the plane including resampled center point 612.

If a typical reconstruction volume of interest 126 has dimensions of 500×500×500 voxels, the number of weights that must be calculated is 500$^3$, or 125 million different voxel weights. Further, this must be done at each projection position $P_i$, which, often, pushes the calculations into the tens of billions. However, making use of the knowledge that the alignment of the v-axis 616 of the resampled detector plane has been constructed to be exactly parallel to the z-axis 320, of the reconstruction volume, a weighting coefficient can be calculated independent of a z-axis 320 offset of each voxel in reconstruction volume of interest 126. This reduces the number of calculations and the resulting size of a table of weighting coefficients by a factor of the length of z-axis 320. FIG. 6B illustrates this further.

In reference to FIG. 6B, SID 628 and SOD 630 are shown again with SOD 630 ending at both z-axis 320 and a new plane, illustrated as plane with constant SOD/SID ratio 636. This plane is parallel to resampled detector plane 610. The voxels in this plane may have different SID 628 and SOD 630 measurements, but all have the same SOD/SID ratio. This is proven geometrically, given the nature of the congruent angles between SOD 630 and plane with constant SOD/SID ratio 636, and SID 628 and resampled detector plane 610. As SID 628 and SOD 630 extend higher or lower, while remaining fixed to radiation source 120 and with respect to resampled detector plane 610, the congruent angles are always equal and, thus, SOD/SID ratios are always equal across plane with constant SOD/SID ratio 636.

Given the nature of plane with constant SOD/SID ratio 636, additional vertical planes can be drawn parallel to resampled detector plane 610 that collectively pass through every voxel in reconstruction volume of interest 126. Each plane has a different SOD/SID ratio, but voxels across each respective plane have the same SOD/SID ratio. Therefore, S offset 624 can be established as intersecting with each vertical plane. The total number of voxels along this synthetic axis represents the maximum number of SOD/SID ratios that must be calculated to calculate the weight of every voxel for this projection $P_i$. A table of weights can be established for each potential value of S offset 624 and stored in digital data processor 116. This significantly reduces the number of calculations that must be performed by digital data processor 116 by a factor of the length of the z-axis 320 of reconstruction volume of interest 126.

FIG. 7 illustrates a method 700 of pre-calculating a weighting coefficient for projection voxels.

Step 710: Moving to Projection Position

In this step, radiation source 120 and detector 122 are aligned at projection position $P_i$ and a CT scan process is executed. Alternatively, those systems performing correction for non-rigid CT-based systems, such as those employing a C-arm, as described in reference to Method 500, may skip this step, as digital data processor 116 already has the necessary data for calculating the weighting coefficient. Method 700 proceeds to step 720.

Step 720: Calculating S-Offset Value

In this step, digital data processor 116 calculates and stores the measured distance from radiation source 120 to the center of each pixel in one (x, y) plane of the reconstruction volume of interest 126, illustrated in FIG. 6A as SOD 630 at each projection angle B. Alternatively, those systems performing correction for non-rigid C-arm-based geometry, as described in reference to Method 500, calculate SOD as the distance of focus from resampled detector plane 610 on S-axis 620, illustrated in FIG. 6A as $f_s$ calculation 632 minus r calculation 634. Method 700 proceeds to step 730.

Step 730: Building Linear Array of w Values for 'S'

In this step, digital data processor 116 calculates a weighting coefficient for each S offset 624 that has a plane with constant SOD/SID ratio 636 and that intersects a part of reconstruction volume of interest 126. In the extreme case, digital data processor 116 could calculate a w entry for each voxel in one of the (x, y) planes of reconstruction volume of interest 126 for each projection. But because the table is fairly linear, digital data processor 116 can create a single linear table that contains about as many entries as the size of either the x or y dimension of reconstruction volume of interest 126, and use the calculated value of S offset 624 to index and interpolate a specific estimate of w. Method 700 proceeds to step 740.

Step 740: Storing w Values

In this step, digital data processor 116 stores a table of calculated weighting coefficients and their respective calculated S offsets 624 in long-term memory (not shown). Method 700 proceeds to step 750.

Step 750: Another Projection?

In this decision step, it is determined whether weight coefficients must be calculated at another projection position $P_i$. If yes, method 700 returns to step 710. If no, method 700 ends.

Figure 8A:
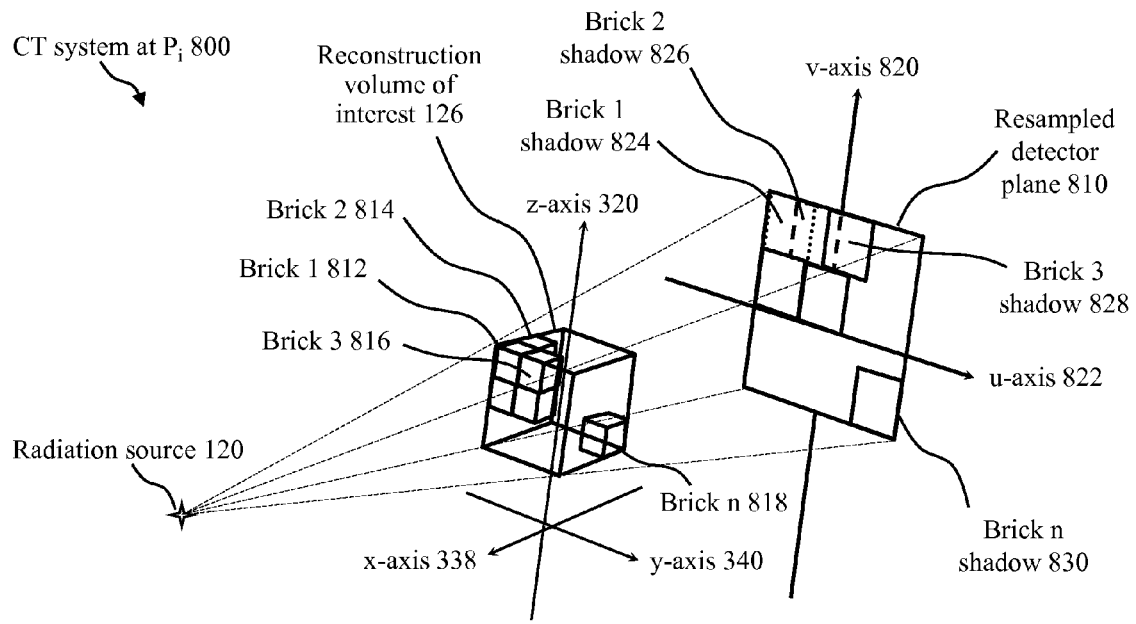
FIG. 8A illustrates an example projection position of a CT system in accordance with one practice of the invention.
Figure 8B:
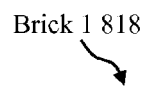
FIG. 8B illustrates details of a brick of a CT system in accordance with one practice of the invention.
Figure 8B:
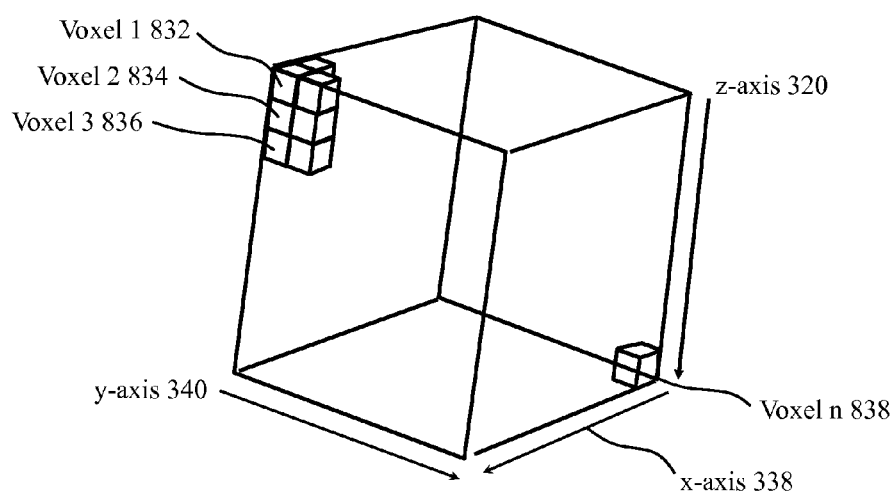
Figure 9:
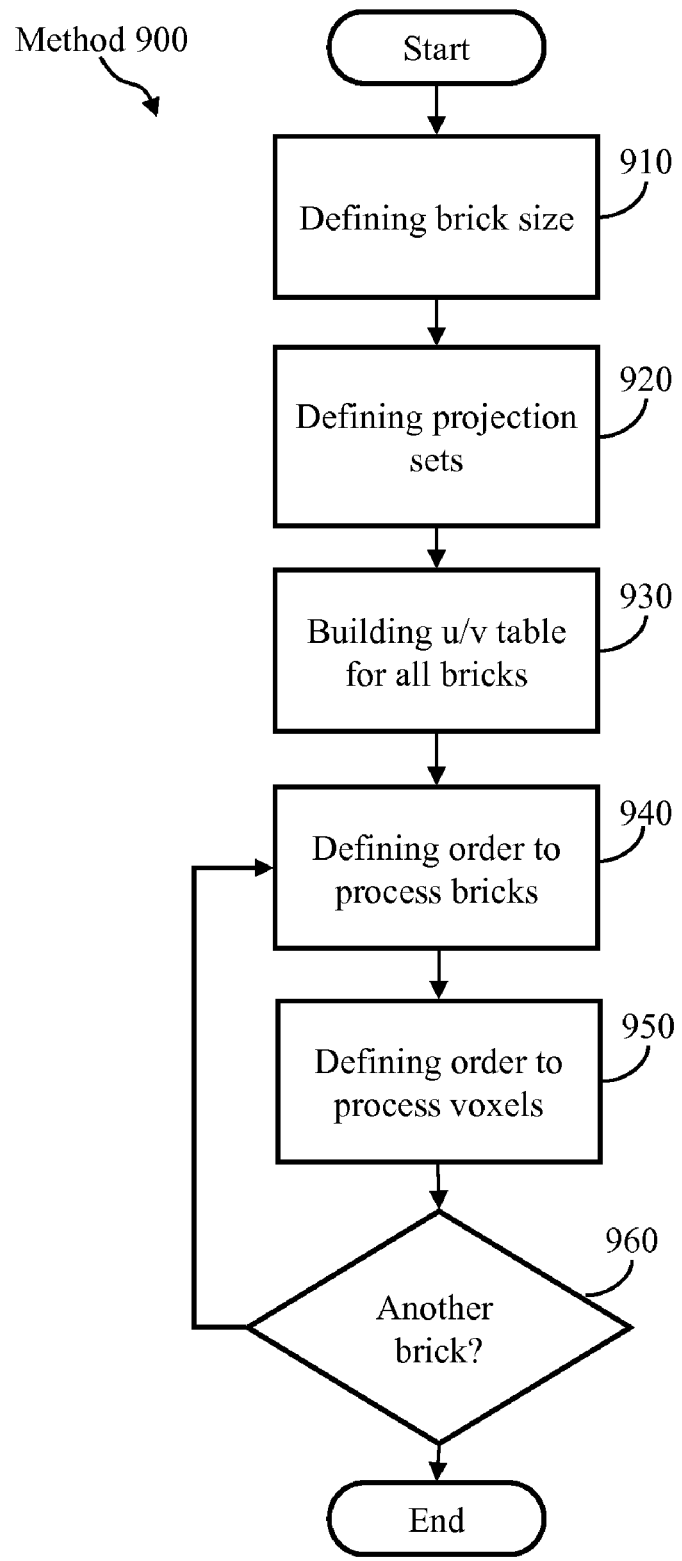
FIG. 9 illustrates a method of pre-calculating the optimal order in which to process individual voxels for backprojection reconstruction in accordance with one practice of the invention.

FIGS. 8A and 8B illustrate system-level diagrams for, and FIG. 9 illustrates a specific method of, pre-calculating the optimal order in which to process individual voxels for backprojection reconstruction, as previously introduced in Steps 230 and 240 of Method 200 of FIG. 2.

FIG. 8A illustrates CT system 100 at $P_i$ 800 and includes a resampled detector plane 810, a brick 1 812, a brick 2 814, a brick 3 816, and a brick n 818. Resampled detector plane 810 further includes a v-axis 820, a u-axis 822, a brick 1 shadow 824, a brick 2 shadow 826, a brick 3 shadow 828, and a brick n shadow 830.

FIG. 8B illustrates further details of brick 1 812 and includes a voxel 1 832, a voxel 2 834, a voxel 3 836, and a voxel n 838.

Ultimately, every voxel in reconstruction volume of interest 126 is calculated as the sum of a function of projection images 112 data, taken from each projection position. Each projection image 112 is large enough so that it is impossible for the fastest memory of digital data processor 116 to hold all projection images 112. An implementation in which voxels are processed in full raster order across the three dimensions results in the reading of data from projection images 112 that is far from optimal from a memory access order standpoint. However, by breaking up reconstruction volume of interest 126 into artificial sub-units, or "bricks", defined as a collection of adjacent voxels, and by processing all of the voxels in one brick before proceeding to another, digital data processor 116 is able to greatly improve the locality of the memory access of projection images 112 data, thus improving the memory access performance of digital data processor 116 by significantly increasing the number of "cache hits" during image reconstruction.

Therefore, an algorithm can be used to pre-calculate an optimal number of bricks into which each reconstruction volume of interest 126 should be divided. This allows CPU 132 or GPU 134 to work on areas of reconstruction volume of interest 126 that project back to projection images 112 in regions that are sequential or near in physical address. As a result, this reduces further the processing time and resources needed for image reconstruction. The projection of each brick is only dependent on the geometry of CT system 100, not on projection images 112 data itself; as such, because the geometry of reconstruction volume of interest 126 is known, the optimal processing order can be calculated prior to an actual CT scan procedure and stored in digital data processor 116. The system does not need actual projection image 112 data of patient or subject of interest 124.

FIG. 8A illustrates that reconstruction volume of interest 126 is broken into individual bricks, as shown by the presence of brick 1 812, brick 2 814, brick 3 816, and brick n 818. The dimensions of the group of bricks are determined by digital data processor 116, according to the size of reconstruction volume of interest 126, number of available pixel shaders 160 in GPU 134 or other processor, and cache size of each pixel shaders 160.

As radiation source 120 projects reconstruction volume of interest 126 onto resampled detector plane 810, there is a geometric correlation between the three-dimensional location of data in reconstruction volume of interest 126 and the two-dimensional projected location on resampled detector plane 810. For example, the top and leftmost voxel within reconstruction volume of interest 126 is projected at the top and leftmost position on resampled detector plane 810. Likewise, for each brick in reconstruction volume of interest 126, the position at which each brick's voxels will be projected as pixels on resampled detector plane 810 also can be calculated. For example, with respect to FIG. 8A, brick 1 812 projects brick 1 shadow 824. While both brick 2 814 and brick 3 816 are adjacent to brick 1 812 in reconstruction volume of interest 126, brick 2 814 projects brick 2 shadow 824 and is, therefore, the next top and leftmost brick on resampled detector plane 810. Note that brick 3 816 would be the next brick to process, which illustrates that a simple rastering pattern of bricks across a single axis would not be optimal. Furthermore, the processing order will vary for each projection position, depending on the orientation of reconstruction volume of interest 126 at each position. Given the aforementioned relationship between voxels and pixels of image data, digital data processor 116 determines the optimal order in which to process bricks, by ordering bricks based on top and leftmost position on resampled detector plane 810. In other embodiments of the invention, the processing order may start at the top and rightmost brick, bottom and leftmost brick, or bottom and rightmost brick.

Note that while projection images 112 appear as a perfect square on resampled detector plane 810 in FIG. 8A for illustrative purposes, a cube-shaped reconstruction volume of interest 126 actually produces a shadow that is the outline of a pair of connected rhombuses, for which the parallel edges are aligned with the vertical axis. In some cases, one rhombus is completely enclosed in the other, so the projection image 112 is a rhombus; in other shapes and/or projection positions, they overlap and produce an irregular hexagon.

It is the nature of the geometry of reconstruction volume of interest 126 that, as a projection position is changed, assuming a very small increment in angular orientation, the calculated optimized order in which to process a set of bricks does not change much, if at all. Therefore, it can be assumed that the optimum order in which to go through a set of bricks at projection position $P_0$ is also nearly optimum for projection $P_1$. As a result, digital data processor 116 can choose n number of projection positions that should have the same brick ordering and only calculate what the brick ordering should be for a single projection. While this does not impact the overall number of calculations that must be performed by GPU 134 on each voxel, it reduces the number of brick processing optimization calculations that must be done on each projection.

This also allows the calculation of voxels from a set of projection images 112 to be calculated in parallel, as illustrated in FIG. 8B. The contribution of each projection image 112 can then be summed and, finally, stored into digital data processor 116 by use of a single "write" operation. For example, if digital data processor 116 determines that each slab in reconstruction volume of interest 126 should be divided into an array of 32×32 bricks, and if each brick contained a matrix of 16×16×8 voxels, this would produce a slab that contained (8) 512×512 voxel planes. Grouping each set of consecutive projections together reduces the number of brick processing optimization calculations by the factor for which they are grouped.

FIG. 9 illustrates a method 900 of pre-calculating the optimal order in which to process individual voxels for back-projection reconstruction.

Step 910: Defining Brick Size

In this step, digital data processor 116 calculates the optimal size in which reconstruction volume of interest 126 should be divided into bricks. This calculation is determined as digital data processor 116 chooses the dimensions of each brick that is a multiple of the number of pixel shaders 160 that will process the bricks, without exceeding the cache limits of each pixel shaders 160. Method 900 proceeds to step 920.

Step 920: Defining Projection Sets

In this step, digital data processor 116 groups the number of projections together, such that a certain number of projections will all receive the same brick processing order. Therefore, digital data processor 116 has to calculate only the optimal processing order for bricks over each projection set, rather than on each projection. Method 900 proceeds to step 930.

Step 930: Building u/v Table for all Bricks

In this step, at each projection position $P_i$, digital data processor 116 calculates u-axis and v-axis coordinates at which each brick in reconstruction volume of interest 126 will be projected onto resampled detector plane 810. This information is then stored as a table in long-term memory (not shown) of digital data processor 116, where the number of tables corresponds to the number of projection positions. The actual projection calculation may be done only at the vertices of each brick. The coordinates of the individual voxels within a brick may be just a linear interpolation between the projected coordinates of the brick's corners. The acceptability of using a linear interpolation is a function of the number of voxels contained in a brick. If the geometric error is unacceptably large, the size of a brick can be reduced. Method 900 proceeds to step 940.

Step 940: Defining Order to Process Bricks

In this step, digital data processor 116 determines the order in which to process bricks for reconstruction. The optimal order is based on each brick's proximity to one another when projected on resampled detector plane 810. In the preferred embodiment of the invention, the brick that casts the uppermost and leftmost projection onto resampled detector plane 810 is chosen first. Note that, while it is always a brick that occupies a corner of the current slab, the specific corner varies, depending on the orientation of reconstruction volume of interest 126 at the current projection angle. With respect to FIG. 8A, this is brick 1 812. Digital data processor 116 determines the optimal order in which to process bricks, by ordering bricks based on top and leftmost position when projected on resampled detector plane 810. Method 900 proceeds to step 950.

Step 950: Defining Order to Process Voxels

In this step, digital data processor 116 determines the order in which to process voxels of each brick for image reconstruction. A primary axis that is designed to occupy consecutive locations in memory of digital data processor 116 is determined first. In the present invention, this is z-axis 820, because voxels along z-axis 820 have the same weighting coefficients as determined in reference to Method 700 and therefore, require only a single read by digital data processor 116. Note that the choice of either x-axis 338 or y-axis 340 to be the next outer loop during processing has little impact on the performance of digital data processor 116. Method 900 proceeds to step 960.

Step 960: Another Brick?

In this decision step, it is determined whether there are additional bricks in reconstruction volume of interest 126 to process. If yes, method 900 returns to step 940. If no, method 900 ends.

Figure 10:
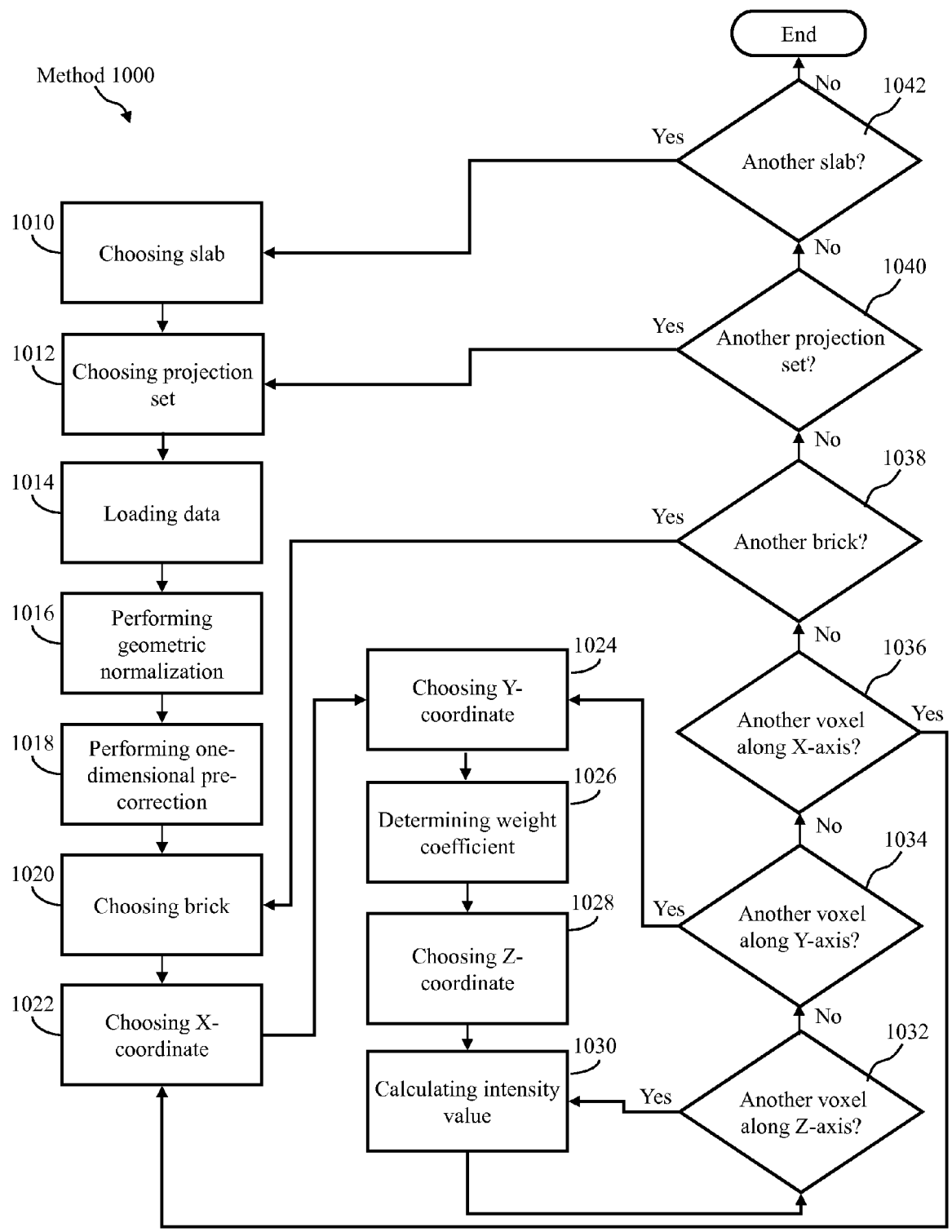
FIG. 10 illustrates a method of performing backprojection image reconstruction in accordance with one practice of the invention.

FIG. 10 illustrates a method 1000 of performing back-projection image reconstruction, as previously introduced in Step 250 of Method 200.

Step 1010: Choosing Slab

In this step, digital data processor 116 chooses a slab, which is defined as a plane of bricks along the same x-axis 338 and y-axis 340 of reconstruction volume of interest 126, to process. For example, brick 1 812, brick 2 814, and brick 3 816 are in the same slab. Digital data processor 116 processes slabs from top to bottom order along z-axis 320 of reconstruction volume of interest 126. Method 1000 proceeds to step 1012.

Step 1012: Choosing Projection Set

In this step, digital data processor 116 chooses the number of projections, or the projection set, for which the remaining calculations of method 1000 will be performed as determined in Step 920. Method 1000 proceeds to step 1014.

Step 1014: Loading Data

In this step, data from projection images 112 of the determined projection set is loaded into GPU 134. The coordinates of the eight corners of the reconstruction slab are projected onto each detector 122. The smallest rectangular area that includes these points is then calculated by digital data processor 116. Because detector 122 is a plane, all voxels within the slab fall within this rectangle. Note that this step may be performed for one captured projection set while a CT scan procedure continues to capture additional projection sets, thus enabling real-time applications of the system. Method 1000 proceeds to step 1016.

Step 1016: Performing Geometric Normalization

In this step, digital data processor 116 performs geometric normalization of the current slab of data. This is a two-dimensional perspective warp calculation, performed either by a general purpose PC, such as digital data processor 116, or by a graphics processing unit, such as GPU 134. Method 1000 proceeds to step 1018.

Step 1018: Performing One-Dimensional Pre-Correction

In this step, digital data processor performs one-dimensional pre-correction for Feldkamp backprojection of the current slab of data. This conventional filter, which is well known in the art, helps correct for the mass distribution errors that are inherent in the use of weighted backprojection as a reconstruction technique. While other algorithms may be used to perform this pre-correction, the preferred embodiment utilizes Shepp-Logan filters. Method 1000 proceeds to step 1020.

Step 1020: Choosing Brick

In this step, digital data processor 116 chooses a brick in the current slab of reconstruction volume of interest 126 to process, based on the order as determined in Step 940 of method 900. This process is further simplified by ordering the u-axis and v-axis projection coordinates of each brick in the u/v table calculated in Step 930 of Method 900, based on the predetermined order for processing. Method 1000 proceeds to step 1022.

Step 1022: Choosing x-Coordinate

In this step, digital data processor 116 chooses an x-coordinate of voxels in the current brick to process, based on the order in which to process voxels of a brick, as determined by method 900. Method 1000 proceeds to step 1024.

Step 1024: Choosing y-Coordinate

In this step, digital data processor 116 chooses a y-coordinate of voxels in the current brick to process, based on the order in which to process voxels of a brick, as determined by method 900. Method 1000 proceeds to step 1026.

Step 1026: Determining Weight Coefficient

In this step, digital data processor 116 determines the weighting coefficient for all voxels along the current x-axis and y-axis, by using S offset 422 of the voxels to find the pre-calculated weighting coefficient stored in digital data processor 116, as described in Method 700. Method 1000 proceeds to step 1028.

Step 1028: Choosing z-Coordinate

In this step, digital data processor 116 chooses a z-coordinate of voxels in the current brick to process, based on the order in which to process voxels of a brick, as determined by method 900. Method 1000 proceeds to step 1030.

Step 1030: Calculating Intensity Value

In this step, digital data processor 116 calculates the intensity value of each voxel along the current z-coordinate for the selected x- and y-coordinates of the current brick. The intensity of each voxel in the reconstruction image is equal to the intensity summation of the same voxel at each projection position, with a u physical coordinate and a v physical coordinate, multiplied by a weighting coefficient. This is illustrated as: $I[x, y, z] = \Sigma_\beta P[u(x, y, \beta), v(x, y, z, \beta),] * w(x, y, \beta)$ where $u=((T-f_u)*SID/(SOD-S))+f_u$ and $v=((z-f_v)*SID/(SOD-S))+f_v$.

By calculating intensities across a set of projections, the number of calculations between reading voxel data from projection images 112 and reading/writing voxel data to a reconstruction is reduced. For example, if there are eight projections in a projection set, a current voxel value, defined as $I[x,y,z]$, is read and written only once for every eight projection calculations. This is especially important in GPU 134 implementations, in which the read/write bandwidth to the recreated image is much lower than the collective read bandwidth of the multiple projection images 112 stored in memory of digital data processor 116. Method 1000 proceeds to step 1032.

Step 1032: Another Voxel on z-Axis?

In this decision step, it is determined whether there is another voxel along the same z-axis of the current brick. If yes, method 1000 returns to step 1030. If no, method 1000 proceeds to step 1034.

Step 1034: Another Voxel on y-Axis?

In this decision step, it is determined whether there is another set of voxels along another y-axis of the current brick to process. If yes, method 1000 returns to step 1024. If no, method 1000 proceeds to step 1036.

Step 1036: Another Voxel on x-Axis?

In this decision step, it is determined whether there is another set of voxels along another x-axis of the current brick to process. If yes, method 1000 returns to step 1022. If no, method 1000 proceeds to step 1038.

Step 1038: Another Brick?

In this decision step, it is determined whether there is another brick in current slab of reconstruction volume of interest 126 to process. If yes, method 1000 returns to step 1020. If no, method 1000 proceeds to step 1040.

Step 1040: Another Projection Set?

In this decision step, it is determined whether there is another projection set for the current set of bricks of the same slab. If yes, method 1000 returns to step 1012. If no, method 1000 proceeds to step 1042.

Step 1042: Another Slab?

In this decision step, it is determined whether there is another slab of reconstruction volume of interest 126 to process. If yes, method 1000 returns to step 1010. If no, method 1000 ends.

The foregoing and other objects are met by the methods and apparatus described above. It will be appreciated that the illustrated embodiment is merely on example of the invention and that other embodiments incorporating one or more of the architectures, modes of operations, methodologies and/or other features described above fall within the scope of the invention. Thus, by way of non-limiting example, it will be appreciated that although the illustrated embodiment is described in respect to certain medical imaging applications, the invention has application beyond the particular applications described, as well as beyond medical imaging itself.

We claim:

1. A method for computed tomography (CT) for calculating mathematical corrections for geometric distortion of a non-rigid CT system, the method comprising:

A. during a calibrating phase, executing the steps of
  (i) calculating a central axis of rotation for a non-circular orbit of a CT scanner using projection positions at which a detector of the CT scanner acquires images of a volume to be reconstructed, where the central axis of rotation is the central axis of a resample circle, the resample circle being the best-fit circle representing the non-circular orbit of the CT scanner based on the projection positions;
  (ii) defining a coordinate system of a reconstruction volume of an object based on the resampled circle comprising an x-axis and a y-axis;
  (iii) calculating a resampled detector plane of the detector of the CT scanner for each projection position, where the resampled detector plane is in a plane tangential to the resampled circle;
  (iv) defining a source-normal ray for each projection position, the source-normal ray being a ray in the same plane as the resampled circle and passing through the center point of the resample circle and intersecting a center point of the resampled detector plane; and
  (v) calculating and storing a projection offset for each projection position based on a comparison of the x-axis and a further axis found at each projection position, the further axis being in the plane of the resampled circle and intersecting the midpoint of the resampled detector plane at each projection position; and B. in a runtime phase,
  i) applying the projection offset calculated in the calibration phase to correct for geometric distortion of projections of an object to be reconstructed acquired with the non-rigid CT system to obtain corrected projections; and
  ii) performing volume reconstruction with the corrected projections, where the reconstruction utilizes a determined order in which to process two or more bricks of the volume to be reconstructed based at least in part on the proximity of said bricks to one another when images of the bricks are projected onto the plane of the detector.

2. The method of claim 1, wherein x-axis and y-axis of the coordinate system in step A(ii) are in a plane aligned with the resampled circle and intersect with a midpoint of the resampled circle.

3. The method of claim 1, wherein the coordinate system of step A(ii) remains fixed with respect to a first projection position.

4. The method of claim 1, wherein the resampled detector plane is determined by a digital data processor and stored in a memory of the digital data processor.

5. The method of claim 1, wherein the projection offset is a function of an angle between the x-axis and the further axis at each projection position.

6. A method for computed tomography (CT) for determining a weighting coefficient for voxels in one or more planes of a reconstructed volume of an object, the method comprising:
   A. during a calibrating phase, executing the steps of
      (i) calculating a distance (SOD) between a radiation source of a CT scanner and a volume to be reconstructed;
      (ii) building a linear array of weighting coefficients (w) for one or more voxels in the volume to be reconstructed using the SOD values calculated in step A(i), wherein $w=[SOD/(SOD-S)]^2$
         wherein $S = x \cos \beta + y \sin \beta$
         wherein $\beta$ is an angle between an x-axis and an S-axis;
         wherein the x-axis is in a plane aligned with the resampled circle and intersect with a midpoint of a resampled circle at a first projection position and wherein the S-axis is in a plane aligned with the resampled circle and intersect with a midpoint of the resampled circle at a further projection position;
      (iii) storing the w values;
      (iv) performing steps A(i) A(ii), and A(iii) for each projection position; and
   B. in a runtime step, applying the w values during reconstruction of the volume to be reconstructed, said reconstruction of the volume to be reconstructed includes determining an order in which to process two or more bricks of the volume to be reconstructed based at least in part on the proximity of said bricks to one another when images of the bricks are projected onto the plane of the detector, wherein each brick comprises voxels.

7. The method of claim 6, wherein the calibrating phase further includes moving and aligning the radiation source and a detector of the CT scanner to each projection position.

8. The method of claim 6, wherein the SOD value is the distance measured between the radiation source and the volume to be reconstructed when the CT scanner has a rigid geometry.

9. The method of claim 6, wherein $SOD=f_s-r$ when the CT scanner has a non-rigid geometry, wherein
   $f_s$ is the distance from the radiation source to a resampled detector plane, and
   r is the distance from a z-axis to a plane including the center point of a resampled detector plane, where the z-axis is an axis passing through the center point of a resampled circle and perpendicular to a plane of the resampled circle,
   wherein the resampled circle is a best-fit circle representing the non-circular orbit of the CT scanner based on each projection position, and
   wherein the resampled detector plane is in a plane tangential to the resampled.

* * * * *